United States Patent
Gosselin et al.

(10) Patent No.: US 9,346,682 B2
(45) Date of Patent: May 24, 2016

(54) SILICA MICROCAPSULES, PROCESS OF MAKING THE SAME AND USES THEREOF

(71) Applicant: LES INNOVATIONS MATERIUM INC., Granby (CA)

(72) Inventors: Mathilde Gosselin, Granby (CA); Shaoyong Yu, Verdun (CA); Nabil Ghezal, Villeneuve-Saint-Georges (FR); Cé Guinto Gamys, Granby (CA)

(73) Assignee: LES INNOVATIONS MATERIUM, Granby, Quebec ( * ) Notice: Subject to any disclaimer, the term of this patent is extended or adjusted under 35 U.S.C. 154(b) by 0 days.

(21) Appl. No.: 14/362,115

(22) PCT Filed: Nov. 30, 2012

(86) PCT No.: PCT/CA2012/001111
§ 371 (c)(1),
(2) Date: May 30, 2014

(87) PCT Pub. No.: WO2013/078551
PCT Pub. Date: Jun. 6, 2013

(65) Prior Publication Data
US 2014/0341958 A1  Nov. 20, 2014

Related U.S. Application Data

(60) Provisional application No. 61/565,576, filed on Dec. 1, 2011, provisional application No. 61/593,509, filed on Feb. 1, 2012, provisional application No. 61/608,121, filed on Mar. 8, 2012, provisional application No. 61/617,057, filed on Mar. 29, 2012.

(51) Int. Cl.
| | | |
|---|---|---|
| C01B 33/12 | (2006.01) | |
| A61K 8/25 | (2006.01) | |
| A61K 8/11 | (2006.01) | |
| B01J 13/18 | (2006.01) | |
| C09B 67/02 | (2006.01) | |
| F28D 20/02 | (2006.01) | |
| A61Q 13/00 | (2006.01) | |
| A61K 8/02 | (2006.01) | |
| C09B 67/46 | (2006.01) | |
| A61K 8/97 | (2006.01) | |
| A61Q 19/00 | (2006.01) | |
| H01B 1/02 | (2006.01) | |
| H01B 1/12 | (2006.01) | |
| A61K 9/50 | (2006.01) | |

(52) U.S. Cl.
CPC ............... *C01B 33/12* (2013.01); *A61K 8/025* (2013.01); *A61K 8/0241* (2013.01); *A61K 8/11* (2013.01); *A61K 8/25* (2013.01); *A61K 8/97* (2013.01); *A61K 9/501* (2013.01); *A61Q 13/00* (2013.01); *A61Q 19/00* (2013.01); *B01J 13/185* (2013.01); *C09B 67/009* (2013.01); *C09B 67/0097* (2013.01); *F28D 20/023* (2013.01); *H01B 1/02* (2013.01); *H01B 1/127* (2013.01); *H01B 1/128* (2013.01); *A61K 2800/412* (2013.01); *Y02E 60/145* (2013.01); *Y10T 428/2989* (2015.01)

(58) Field of Classification Search
None
See application file for complete search history.

(56) References Cited

U.S. PATENT DOCUMENTS

| | | | |
|---|---|---|---|
| 4,671,909 A | 6/1987 | Torobin | |
| 2006/0019098 A1 | 1/2006 | Chan et al. | |
| 2009/0252809 A1* | 10/2009 | Galeone et al. | 424/497 |
| 2010/0310872 A1* | 12/2010 | Nakamura | 428/405 |
| 2011/0150954 A1* | 6/2011 | Lapidot et al. | 424/401 |
| 2011/0229576 A1* | 9/2011 | Trogler et al. | 424/490 |
| 2012/0295790 A1* | 11/2012 | Yan et al. | 504/273 |

FOREIGN PATENT DOCUMENTS

| | | | |
|---|---|---|---|
| CN | 101708853 A | 5/2010 | |
| EP | 2078696 A1 | 7/2009 | |
| WO | WO-2004/081222 A2 | 9/2004 | |
| WO | WO-2008/002637 A2 | 1/2008 | |
| WO | WO-2011/081787 A2 | 7/2011 | |
| WO | WO 2011081787 A2 * | 7/2011 | ............. A01N 25/28 |

OTHER PUBLICATIONS

International Search Report received for PCT Patent Application No. PCT/CA2012/001111, mailed on Mar. 8, 2013, 3 pages.
International Preliminary Report on Patentability received for PCT Patent Application No. PCT/CA2012/001111, mailed on Feb. 23, 2014, 15 pages.
English Abstract of CN101708853; Published May 29, 2010; Retrieved from Espacenet.com on Oct. 14, 2015.
Supplementary European Search Report of corresponding application No. 12853201.7; Jul. 20, 2015; Shane McDonnell; The Hage.
Zhang et al. "Fabrication of microencapsulated phase change materials based on-octadecane core and silica shell through interfacial polycondensation" Colloids and Surfaces A: Physicochemical and Engineering Aspects, vol. 389, No. 1, 2011, pp. 104-117.

\* cited by examiner

*Primary Examiner* — H. Sarah Park
(74) *Attorney, Agent, or Firm* — Morrison & Foerster LLP

(57) ABSTRACT

The present document describes a microcapsule having silica shells, processes for making the same, processes for functionalizing said microcapsules and processes for encapsulating active agent in said microcapsules.

20 Claims, 5 Drawing Sheets

SILICA MICROCAPSULES, PROCESS OF MAKING THE SAME AND USES THEREOF

CROSS-REFERENCE TO RELATED APPLICATIONS

This application is a U.S. national phase of International Application under 35 USC §371 of PCT/CA2012/001111, filed Nov. 30, 2012, which claims priority from and the benefit of, under 35 USC 119(e), of US provisional patent applications U.S. 61/565,576, filed 1 Dec. 2011; 61/593,509, filed 1 Feb. 2012; 61/608,121, filed 8 Mar. 2012; and 61/617,057, filed 29 Mar. 2012, the specifications of which are hereby incorporated by reference, in their entireties.

BACKGROUND (a) Field

The subject matter disclosed generally relates to microcapsules and processes of making the same. More specifically, the subject matter disclosed relates to silica microcapsule and processes for making the same.

(b) Related Prior Art

Compared with traditional organic materials, inorganic matrices and more specifically ceramics have many intrinsic advantages. In particular, they are biologically inert, intrinsically hydrophilic, and represent higher mechanical strength and thermal stability.

Hollow silicon microcapsules are often synthesized using a templating method (such as disclosed in Chinese patent application No. CN 101708853A) where polysterol polymers (e.g. polystyrene) microballoons are used as templates, and usually yield spheres having diameters of about 500 nm to about 4 µm, which are on the smaller scale for such microspheres The inventors have developed a range of processes for making microcapsules based on forming ceramic particles using oil-in-water emulsion and sol-gel processes and related technology for the production of hollow microspheres in the range of 0.1 µm to about 1500 µm. The microcapsules of the present invention may be used as density-reducing additive with extremely low density, as low as 0.001 g/cm$^3$, was invented by taking the form of micron-scale core/shell/functional surface type microcapsules, intent on being used in the plastics, composites, rubbers and textiles industries at little or no cost to their performance. The reduction in density or weight lowers the cost of material and transportation. The present invention relates to core/shell/functional surface type reservoirs or microcapsules, which comprise a core (gaseous or hollow) surrounded by a shell (generally solid) composed essentially of one or more silica-based materials and capped with a functional surface with affinity or adhesion to the matrix of plastics or composites or rubbers or textiles. The present invention is introduced into plastics, composites, rubbers and textiles products in their processing stage. Gaseous or hollow microcapsules are dispersed throughout or partially in plastics, composites, rubbers and textiles products as a density-reducing additive to reduce the density of the final products.

SUMMARY

According to an embodiment, there is provided a microcapsule comprising:
a silica shell having a thickness of from about 50 nm to about 500 µm, said shell forming a capsule having a diameter from about 0.1 µm to about 1500 µm, and having a density of about 0.001 g/cm$^3$ to about 1.0 g/cm$^3$,
wherein said shell comprises from about 0% to about 70% Q3 configuration, and from about 30% to about 100% Q4 configuration, or
wherein said shell comprises from about 0% to about 60% T2 configuration and from about 40% to about 100% T3 configuration, or
wherein said shell comprises a combination of T and Q configurations thereof, and
wherein an exterior surface of said capsule is covered by a functional group.

The shell may comprise from about 40% Q3 configuration and about 60% Q4 configuration.

The shell may comprise from about 100% Q4 configuration.

The shell may further comprise a plurality of pores.

The pores may have pore diameters from about 0.5 nm to about 100 nm.

The microcapsule may be further comprising a surface layer.

The surface layer may comprise a thickness from about 1 nm to about 10 nm, using a post-functionalization method.

The surface layer may be functionalized with an organosilane.

The organosilane may be chosen from a functional trimethoxysilane, a functional triethoxysilane, a functional tripropoxysilane.

The organosilane may be chosen 3-aminopropyltriethoxysilane, vinyltriacetoxy silane, vinyltrimethoxysilane, 3-glycidoxypropyltrimethoxysilane, 3-methacryloxypropyltrimethoxysilane, 3-chloropropyltriethoxysilane, bis-(triethoxysilylpropyl)tetrasulfane, methyltriethoxysilane, n-octyltriethoxysilane, and phenyltrimethoxysilane and combinations thereof.

The surface layer may be functionalized with a hydroxyl group, an amino group, a benzylamino group, a chloropropyl group, a disulfide group, an epoxy group, a mercapto group, a methacrylate group, a vinyl group, and combinations thereof.

The microcapsule may have a melting point from about 1600° C. to about 1725° C.

The microcapsule may be further comprising a conductive layer surrounding said exterior surface of said capsule.

The conductive layer may be a metallic layer, or a conductive polymer layer.

The metallic layer may be a layer of silver (Ag), gold (Au), copper (Cu), aluminum (Al), or combinations thereof.

The conductive polymer layer is a layer of polypyrrole, polythiophene, polyanilines or combinations thereof.

The microcapsule may be further comprising an active agent.

The active agent may be chosen from a catalyst for monomers polymerization, a polymer stabilizer chemical, a fire retardant chemical, a colorant, a pharmaceutically active drug, an enzyme, a cosmetic oil, a fragrance, a perfume, a food additives, an humidifier, an explosive, a phase change material (PCM), an insecticide, an herbicide, a fungicide and combinations thereof.

The polymer stabilizer chemical may be chosen from butylated hydroxytoluene (BHT), α-tocopherol, tocopheryl acetate, an organophosphate, Tris(2,4-di-tert-butylphenyl) phosphite, trisnonylphenyl phosphite, dilauryl thiodipropionate, distearyl thiodipropionate, Bis(2,2,6,6-tetramethyl-4-piperidyl)sebacate, benzotriazole, benzophenone and combinations thereof.

The fire retardant chemical may be chosen from tetrabromobisphenol-A, decabromodiphenylethane, dibromoneopentylglycol, or combinations thereof.

The colorant may be chosen from carbon black, molybdate orange, chrome oxide green, anthanthrone, anthraquinone, benzimidazole, and quinacridone.

The active agent may be crosslinked to said surface layer, to said exterior surface, or both.

The active agent is encapsulated in said microcapsule.

The microcapsule may have the NMR spectrum as shown in FIG. 1.

According to another embodiment, there is provided a process for the preparation of a microcapsule comprising step a):
 a) contacting with an acidic or alkali catalyst an emulsion formed between a water phase comprising water, an alcohol and one or more surfactants, and an oil phase comprising a silica precursor and a hydrophobic solvent or an oil, for a time sufficient and at a temperature sufficient obtain a formed microcapsule in a liquid phase.

The process may be further comprising step b) after step a):
 b) washing said formed microcapsule to remove said acidic or alkali catalyst, said surfactant and said oil, to obtain washed microcapsules.

The process may be further comprising step c) after step b):
 c) separating said formed microcapsule from said liquid phase.

The process may be further comprising step d) after step c):
 d) drying said washed microcapsules to obtain dried microcapsules.

The drying may be by calcining said formed microcapsule to obtain dried microcapsule at about 200° C. to about 800° C.

The drying may be by forced convection including spray drying, flash drying, fluidized bed drying; or freeze drying said formed microcapsule to obtain dried microcapsule.

The process may be further comprising step e) after step d):
 e) thermal annealing said dried microcapsule at 700° C. to less than about 1100° C.

The may be further comprising reacting said formed microcapsule with a functionalizing reagent to functionalize a surface of said formed microcapsule.

The oil phase comprises said silica precursor and said hydrophobic solvent or said oil in a weight ratio of about 4:1 to about 1:10 (silica precursor:oil or solvent ratio).

The hydrophobic solvent may be chosen from hexane, heptanes, cyclohexane, pentane, cyclopentane, toluene, decalin, benzene, carbon tetrachloride, cyclohexane, 1,4 dioxane and chloroform and combinations thereof.

The oil may be a vegetable oil.

The vegetal oil may be chosen from palm oil, soybean oil, rapeseed oil, sunflower seed oil, peanut oil, cottonseed oil, palm kernel oil, coconut oil, corn oil, grape seed oil, hazelnut oil, linseed oil, rice bran oil, safflower oil, sesame oil, olive oil and combinations thereof.

The silica precursor may be chosen from one or more silanes having 1, 2, 3 or 4 hydrolysable groups per molecule.

The silane may be chosen from a methoxysilane, an ethoxysilane, a propoxysilane, an isopropoxysilane, an aryloxysilane, tetramethoxysilane (TMOS), tetraethoxysilane (TEOS), tetrapropoxysilane (TPOS) or a functional trimethoxy, triethoxysilane, tripropoxysilane including aminopropylsilane, aminoethylaminopropylsilane, vinyltrimethoxysilane, 3-chloropropyltriethoxysilane, 3-glycidoxypropyltrimethoxysilane, methacryloyloxypropyltrimethoxysilane, phenyltriethoxysilane, phenyltrimethoxysilane, glycidoxypropoxytrimethoxysilane, glycidoxypropyltriethoxysilane, mercaptopropyltriethoxysilane, mercaptopropyltrimethoxysilane, aminopropyltrimethoxysilane, 3-aminopropyltriethoxysilane, 3-(2-aminoethylamino)propyltrimethoxysilane, 3-[2-(2-aminoethylamino)ethylamino]propyltrimethoxysilane, [2(cyclohexenyl)ethyl]triethoxysilane, vinyltrimethoxysilane, vinyltriethoxysilane or a mixture of any two or more of the above.

The organo-reactive silane for post-functionalization may be chosen from a functional trimethoxysilane, a functional triethoxysilane, and a functional tripropoxysilane.

The water phase comprising water, said alcohol and said surfactant comprises water and said alcohol in a weight ratio from about 1:100 to 1:4 (alcohol:water ratio)

The alcohol may be chosen from methanol, ethanol, propanol, glycerol, glycol or combinations thereof.

The surfactant may be chosen from a PEO/PPO copolymer (pluronic P123), sorbitan monooleate (Span 80), sorbitan trioleate (Span 85), sorbitan tristearate (Span 65) or sorbitan sesquioleate, sorbitan monolaurate (Span 20), a PEO/PPO copolymer, glycerol monooleate, Tween 20 (polysorbate 20), Tween 80 (polysorbate 80), polysorbate 61 (Tween 61), cetyl trimethylamonium bromide (CTAB), sodium dodecyl sulfate (SDS), a polyoxyethylene fatty ether (Brij30), a nonylphenoxypolyethoxyethanol, an octylphenoxypolyethoxyethanol and combinations thereof.

The surfactant may be in a concentration from about 0.05 mM to about 15 mM.

The acid catalyst may be chosen from HCl, acetic acid, and sulfuric acid.

The alkali catalyst may be chosen from sodium hydroxide, potassium hydroxide or ammonia.

The time sufficient is chosen from about 30 minutes to about 18 hours.

The temperature sufficient may be chosen from room temperature (24° C.) to about 50° C.

According to another embodiment, there is provided a microcapsule prepared according to the process of the present invention.

According to another embodiment, there is provided a process for the post-functionalization in solution of a microcapsule according to the present invention comprising step a):
 a) dispersion, under inert atmosphere, of the dried silica microcapsules in a dried organic solvent in the presence of one or more organo-reactive silanes and an organic acid or an organic base for a time sufficient and at a temperature sufficient obtain a functionalized microcapsule in a liquid dispersion.

The dried organic solvent may comprise dichloromethane, tetrahydrofuran, ethyl acetate, or combinations thereof.

The organic acid may be a carboxylic acid.

The organic base may be an amine base.

The process may further comprise step b) after step a):
 b) separating said functionalized microcapsule from said liquid dispersion.

The process may be further comprising step c) after step b):
 c) drying said functionalized microcapsule to obtain a dried functionalized microcapsule.

The time sufficient may be from about 12 to 24 hours.

The temperature sufficient may be from about 20° C. to about 50° C.

The drying may be at about 30° C. to about 120° C., under vacuum or at a normal pressure or using a spray drying system.

According to another embodiment, there is provided a process for the post-functionalization in solid state of a microcapsule according to the present invention wherein said functionalization is by treating the dried microcapsules with an organosilane vapor.

The microcapsule of the present invention having an NMR spectrum as shown in FIG. 1.

According to another embodiment, there is provided a process for the preparation of a microcapsule encapsulating an active agent comprising step a):

a) contacting with an acidic or alkali catalyst an emulsion formed between a water phase comprising water, an alcohol and one or more surfactants, and an oil phase comprising a silica precursor and a hydrophobic solvent or an oil, for a time sufficient and at a temperature sufficient obtain a formed microcapsule in a liquid phase.

The process may be further comprising step b) after step a):

b) washing said formed microcapsule to remove said acidic or alkali catalyst, said surfactant and said oil, to obtain washed microcapsules.

The process may be further comprising step c) after step b):

c) separating said formed microcapsule from said liquid phase.

The process may be further comprising step d) after step c):

d) drying said washed microcapsules at a temperature sufficient to dry said washed microcapsule without destroying the active agent encapsulated therein, to obtain dried microcapsules.

The drying may be by heating with pressure, heating without pressure, freeze drying, or combinations thereof.

The following terms are defined below.

The term "post-functionalization" or "post-functionalization method" is intended to mean that the functionalization of the microcapsules of the present invention is performed after formation of the microcapsule, by depositing a layer of material onto the surface of the microcapsule that will provide reactive groups to the surface.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

It will be noted that throughout the appended drawings, like features are identified by like reference numerals.

DETAILED DESCRIPTION

Figure 1:
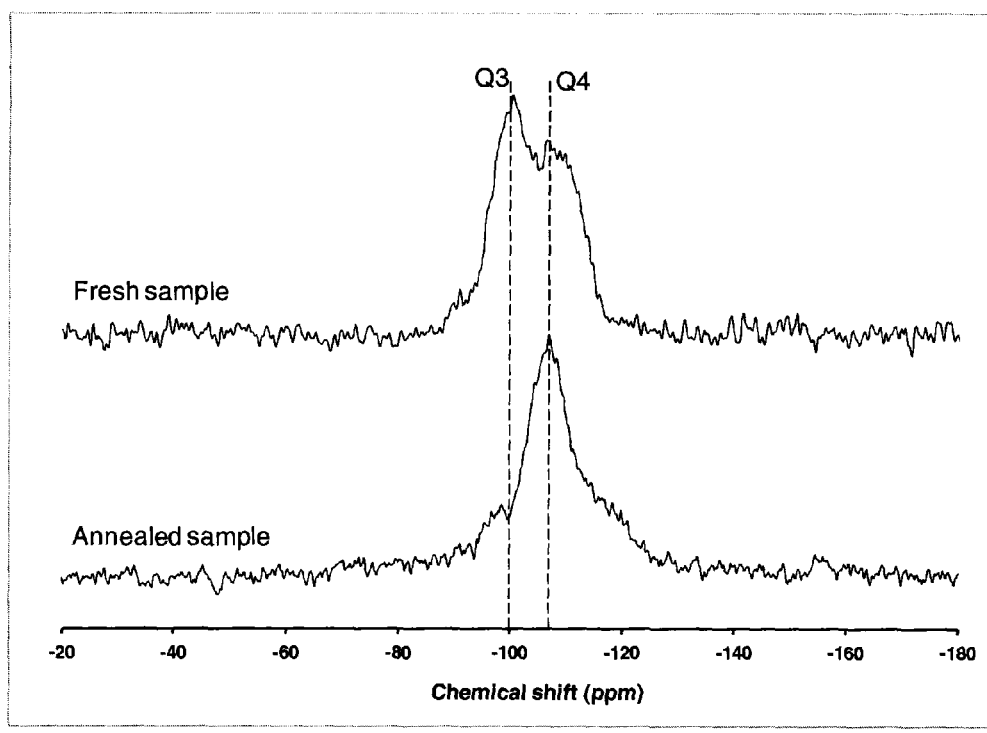
FIG. 1 illustrates the NMR spectrum of microcapsules according to the present invention.
Figure 2:
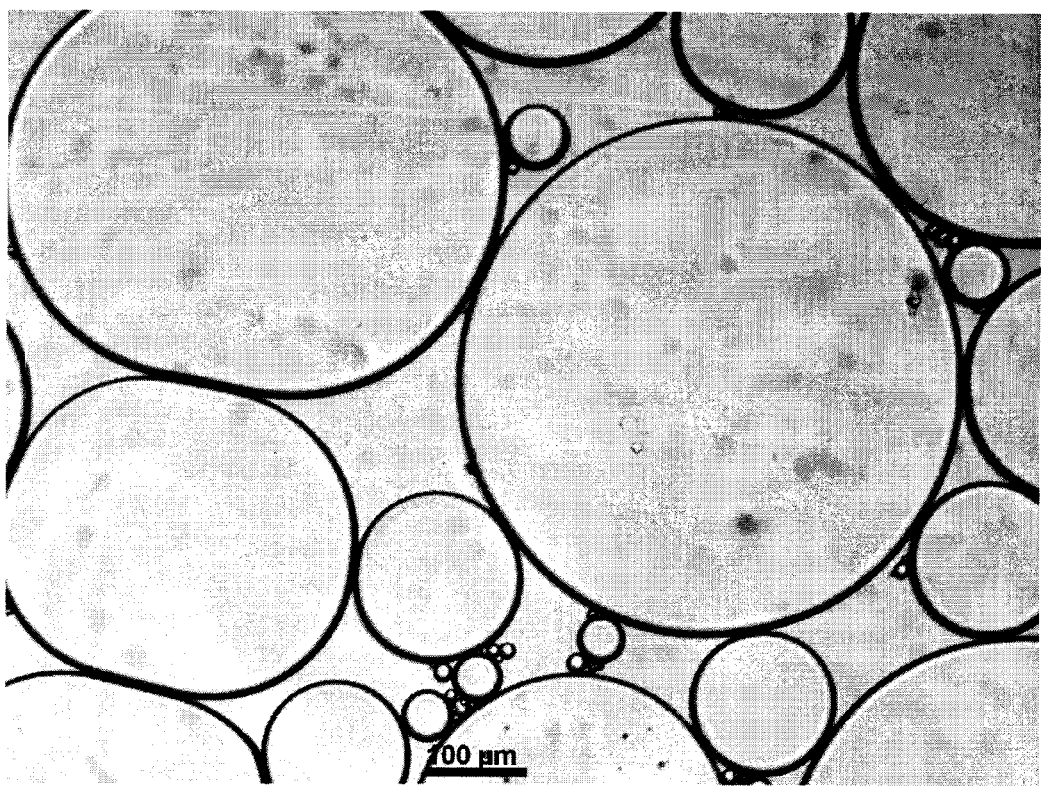
FIG. 2 illustrates optical micrographs of silica microcapsules according to the present invention, obtained from typical synthesis conditions described in example 1.
Figure 3:
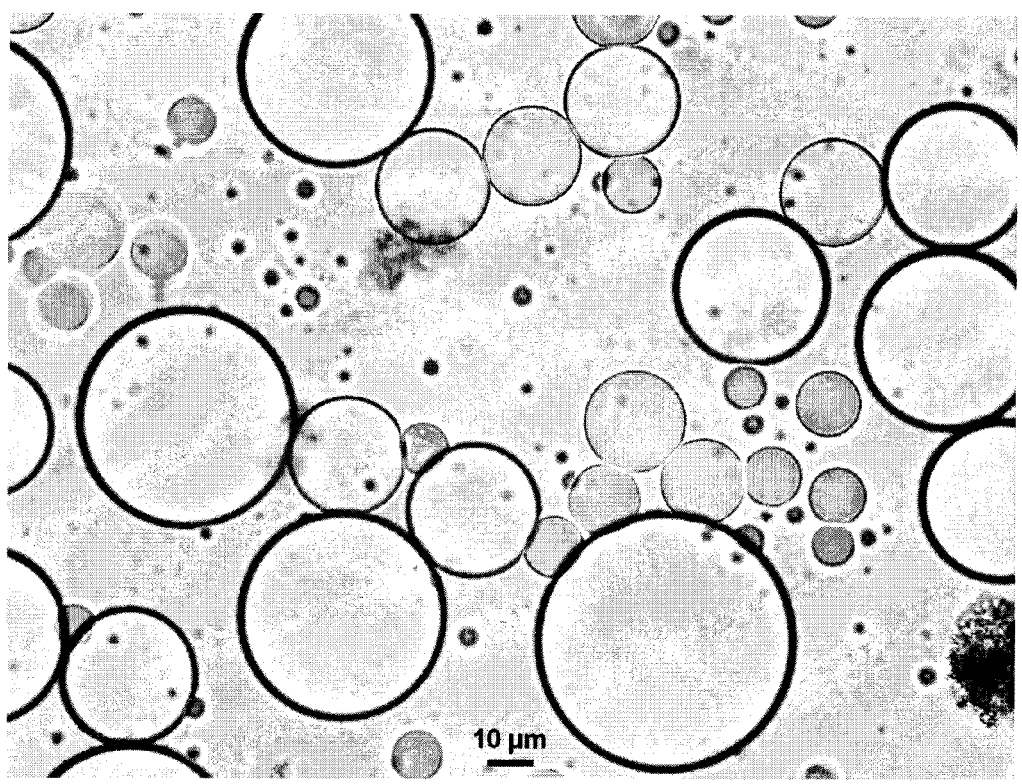
FIG. 3 illustrates optical micrograph of silica microcapsules according to the present invention, obtained from typical synthesis conditions described in example 2.
Figure 4:
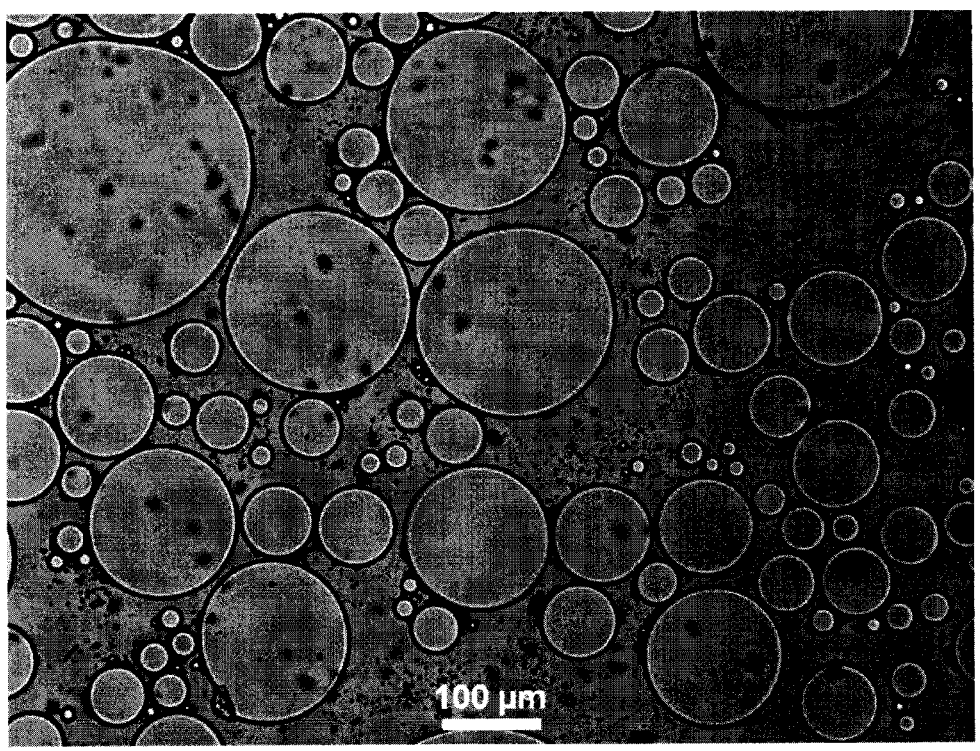
FIG. 4 illustrates optical micrograph of silica microcapsules according to the present invention, obtained from typical synthesis conditions described in example 3.
Figure 5:
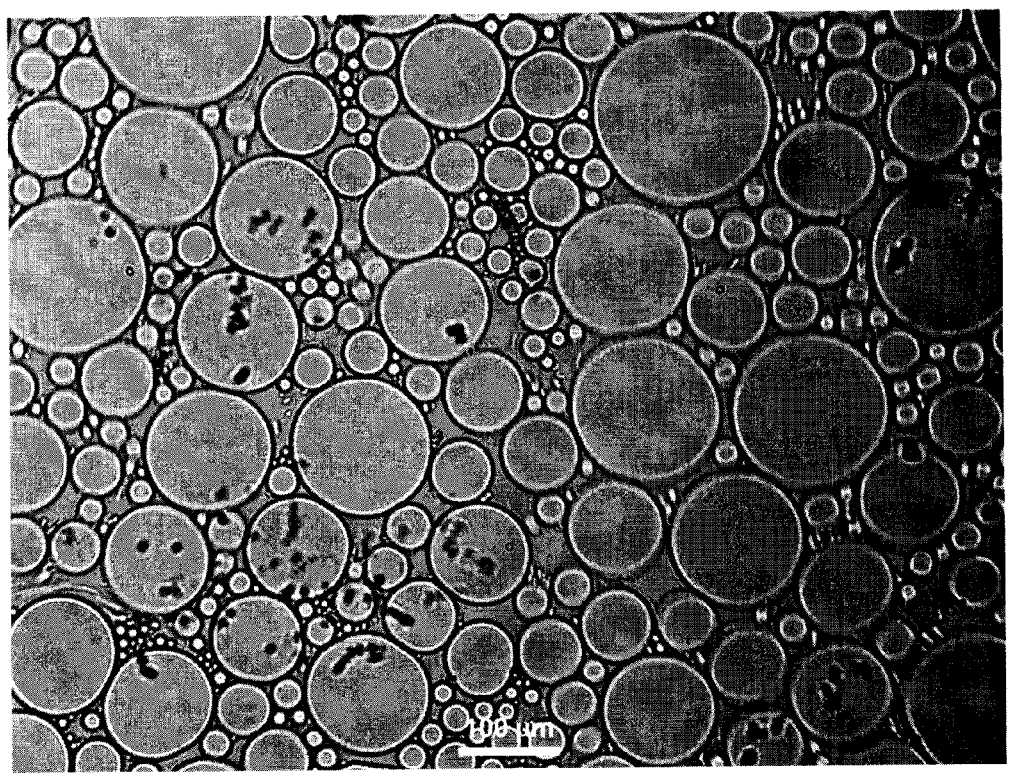
FIG. 5 illustrates optical micrograph of silica microcapsules according to the present invention, obtained from typical synthesis conditions described in example 4.

In a first embodiments there is disclosed a microcapsule comprising
a silica shell having a thickness of from about 50 nm to about 500 μm, the shell forming a capsule having a diameter from about 0.1 μm to about 1500 μm, and having a density of about 0.001 g/cm$^3$ to about 1.0 g/cm$^3$, wherein the structural arrangement of silicon atoms in the shell comprises from about 0% to about 70% Q3, and from about 30% to about 100% Q4, or
wherein the structural arrangement of silicon atoms in the shell comprises from about 0% to about 60% T2 silicon configuration and from about 40% to about 100% T3 silicon configuration or
wherein said shell comprises combinations of T and Q configurations thereof, and
wherein an exterior surface of said capsule is covered by a functional group.

In a second embodiment there is disclosed a process for the preparation of a microcapsule which comprises step a)
a) contacting with an acidic or alkali catalyst an emulsion formed between a mixture comprising water, an alcohol and one or more surfactants, and a homogeneous solution comprising a silica precursor and a hydrophobic solvent or an oil, for a time sufficient and at a temperature sufficient obtain a formed microcapsule in a liquid phase.

Microcapsules

According to the first embodiment there is disclosed a novel density-reducing additive intended to be used in plastics, composites, rubbers and textiles materials and products by employing an extremely low density micron-scale material. The structure is formed by a sequent one-step sol-gel process.

The present invention takes the form of microcapsules with a core/shell/functional surface structure. The core of the microcapsule may be gaseous, hollow or even a vacuum; the shell is composed of silica, which is solid state. Preferably, the silica precursor having been used for fabrication of the microcapsule is chosen, without limitations from one or a combination of silanes having 1, 2, 3 or 4 hydrolysable groups per molecule, provided that at least one of the silanes in the mixture has at least 3 hydrolysable groups per molecule. The hydrolysable groups may be alkoxy groups (e.g. methoxy, ethoxy, propoxy, isopropoxy) or may be aryloxy groups (e.g. phenoxy), or some other hydrolysable groups. It may be for example tetramethoxysilane (TMOS), tetraethoxysilane (TEOS), tetrapropoxysilane (TPOS) or a functional trimethoxy, triethoxy or tripropoxysilane, such as aminopropylsilane, aminoethylaminopropylsilane, vinyltrimethoxysilane, 3-chloropropyltriethoxysilane, or 3-glycidoxypropyltrimethoxysilane, and combinations thereof.

The microcapsules of the present invention have an average diameter from about 0.1 μm to about 1500 μm. The diameter of the microcapsule may be from about 0.1 μm to about 1500 μm, or from about 0.1 μm to about 1000 μm, or from about 0.1 μm to about 1500 μm, or from about 0.1 μm to about 900 μm, or from about 0.1 μm to about 800 μm, or from about 0.1 μm to about 700 μm, or from about 0.1 μm to about 600 μm, or from about 0.1 μm to about 500 μm, or from about 0.1 μm to about 400 μm, or from about 0.1 μm to about 300 μm, or from about 0.1 μm to about 200 μm, or from about 0.1

μm to about 100 μm, or from about 0.1 μm to about 90 μm, or from about 0.1 μm to about 80 μm, or from about 0.1 μm to about 70 μm, or from about 0.1 μm to about 60 μm, or from about 0.1 μm to about 50 μm, or from about 0.1 μm to about 40 μm, or from about 0.1 μm to about 30 μm, or from about 0.1 μm to about 20 μm, or from about 0.1 μm to about 15 μm, or from about 0.1 μm to about 10 μm, or from about 0.1 μm to about 5 μm, or from about 0.1 μm to about 2 μm, 0.5 μm to about 1500 μm, or from about 0.5 μm to about 1000 μm, or from about 0.5 μm to about 1500 μm, or from about 0.5 μm to about 900 μm, or from about 0.5 μm to about 800 μm, or from about 0.5 μm to about 700 μm, or from about 0.5 μm to about 600 μm, or from about 0.5 μm to about 500 μm, or from about 0.5 μm to about 400 μm, or from about 0.5 μm to about 300 μm, or from about 0.5 μm to about 200 μm, or from about 0.5 μm to about 100 μm, or from about 0.5 μm to about 90 μm, or from about 0.5 μm to about 80 μm, or from about 0.5 μm to about 70 μm, or from about 0.5 μm to about 60 μm, or from about 0.5 μm to about 50 μm, or from about 0.5 μm to about 40 μm, or from about 0.5 μm to about 30 μm, or from about 0.5 μm to about 20 μm, or from about 0.5 μm to about 15 μm, or from about 0.5 μm to about 10 μm, or from about 0.5 μm to about 5 μm, or from about 0.5 μm to about 2 μm, 1 μm to about 1500 μm, or from about 1 μm to about 1000 μm, or from about 1 μm to about 1500 μm, or from about 1 μm to about 900 μm, or from about 1 μm to about 800 μm, or from about 1 μm to about 700 μm, or from about 1 μm to about 600 μm, or from about 1 μm to about 500 μm, or from about 1 μm to about 400 μm, or from about 1 μm to about 300 μm, or from about 1 μm to about 200 μm, or from about 1 μm to about 100 μm, or from about 1 μm to about 90 μm, or from about 1 μm to about 80 μm, or from about 1 μm to about 70 μm, or from about 1 μm to about 60 μm, or from about 1 μm to about 50 μm, or from about 1 μm to about 40 μm, or from about 1 μm to about 30 μm, or from about 1 μm to about 20 μm, or from about 1 μm to about 15 μm, or from about 1 μm to about 10 μm, or from about 1 μm to about 5 μm, or from about 1 μm to about 2 μm, 2 μm to about 1500 μm, or from about 2 μm to about 1000 μm, or from about 2 μm to about 1500 μm, or from about 2 μm to about 900 μm, or from about 2 μm to about 800 μm, or from about 2 μm to about 700 μm, or from about 2 μm to about 600 μm, or from about 2 μm to about 500 μm, or from about 2 μm to about 400 μm, or from about 2 μm to about 300 μm, or from about 2 μm to about 200 μm, or from about 2 μm to about 100 μm, or from about 2 μm to about 90 μm, or from about 2 μm to about 80 μm, or from about 2 μm to about 70 μm, or from about 2 μm to about 60 μm, or from about 2 μm to about 50 μm, or from about 2 μm to about 40 μm, or from about 2 μm to about 30 μm, or from about 2 μm to about 20 μm, or from about 2 μm to about 15 μm, or from about 2 μm to about 10 μm, or from about 2 μm to about 5 μm, 3 μm to about 1500 μm, or from about 3 μm to about 1000 μm, or from about 3 μm to about 1500 μm, or from about 3 μm to about 900 μm, or from about 3 μm to about 800 μm, or from about 3 μm to about 700 μm, or from about 3 μm to about 600 μm, or from about 3 μm to about 500 μm, or from about 3 μm to about 400 μm, or from about 3 μm to about 300 μm, or from about 3 μm to about 200 μm, or from about 3 μm to about 100 μm, or from about 3 μm to about 90 μm, or from about 3 μm to about 80 μm, or from about 3 μm to about 70 μm, or from about 3 μm to about 60 μm, or from about 3 μm to about 50 μm, or from about 3 μm to about 40 μm, or from about 3 μm to about 30 μm, or from about 3 μm to about 20 μm, or from about 3 μm to about 15 μm, or from about 3 μm to about 10 μm, or from about 3 μm to about 5 μm, 4 μm to about 1500 μm, or from about 4 μm to about 1000 μm, or from about 4 μm to about 1500 μm, or from about 4 μm to about 900 μm, or from about 4 μm to about 800 μm, or from about 4 μm to about 700 μm, or from about 4 μm to about 600 μm, or from about 4 μm to about 500 μm, or from about 4 μm to about 400 μm, or from about 4 μm to about 300 μm, or from about 4 μm to about 200 μm, or from about 4 μm to about 100 μm, or from about 4 μm to about 90 μm, or from about 4 μm to about 80 μm, or from about 4 μm to about 70 μm, or from about 4 μm to about 60 μm, or from about 4 μm to about 50 μm, or from about 4 μm to about 40 μm, or from about 4 μm to about 30 μm, or from about 4 μm to about 20 μm, or from about 4 μm to about 15 μm, or from about 4 μm to about 10 μm, or from about 4 μm to about 5 μm, 5 μm to about 1500 μm, or from about 5 μm to about 1000 μm, or from about 5 μm to about 1500 μm, or from about 5 μm to about 900 μm, or from about 5 μm to about 800 μm, or from about 5 μm to about 700 μm, or from about 5 μm to about 600 μm, or from about 5 μm to about 500 μm, or from about 5 μm to about 400 μm, or from about 5 μm to about 300 μm, or from about 5 μm to about 200 μm, or from about 5 μm to about 100 μm, or from about 5 μm to about 90 μm, or from about 5 μm to about 80 μm, or from about 5 μm to about 70 μm, or from about 5 μm to about 60 μm, or from about 5 μm to about 50 μm, or from about 5 μm to about 40 μm, or from about 5 μm to about 30 μm, or from about 5 μm to about 20 μm, or from about 5 μm to about 15 μm, or from about 5 μm to about 10 μm, 10 μm to about 1500 μm, or from about 10 μm to about 1000 μm, or from about 10 μm to about 1500 μm, or from about 10 μm to about 900 μm, or from about 10 μm to about 800 μm, or from about 10 μm to about 700 μm, or from about 10 μm to about 600 μm, or from about 10 μm to about 500 μm, or from about 10 μm to about 400 μm, or from about 10 μm to about 300 μm, or from about 10 μm to about 200 μm, or from about 10 μm to about 100 μm, or from about 10 μm to about 90 μm, or from about 10 μm to about 80 μm, or from about 10 μm to about 70 μm, or from about 10 μm to about 60 μm, or from about 10 μm to about 50 μm, or from about 10 μm to about 40 μm, or from about 10 μm to about 30 μm, or from about 10 μm to about 20 μm, or from about 10 μm to about 15 μm, 15 μm to about 1500 μm, or from about 15 μm to about 1000 μm, or from about 15 μm to about 1500 μm, or from about 15 μm to about 900 μm, or from about 15 μm to about 800 μm, or from about 15 μm to about 700 μm, or from about 15 μm to about 600 μm, or from about 15 μm to about 500 μm, or from about 15 μm to about 400 μm, or from about 15 μm to about 300 μm, or from about 15 μm to about 200 μm, or from about 15 μm to about 100 μm, or from about 15 μm to about 90 μm, or from about 15 μm to about 80 μm, or from about 15 μm to about 70 μm, or from about 15 μm to about 60 μm, or from about 15 μm to about 50 μm, or from about 15 μm to about 40 μm, or from about 15 μm to about 30 μm, or from about 15 μm to about 20 μm, 20 μm to about 1500 μm, or from about 20 μm to about 1000 μm, or from about 20 μm to about 1500 μm, or from about 20 μm to about 900 μm, or from about 20 μm to about 800 μm, or from about 20 μm to about 700 μm, or from about 20 μm to about 600 μm, or from about 20 μm to about 500 μm, or from about 20 μm to about 400 μm, or from about 20 μm to about 300 μm, or from about 20 μm to about 200 μm, or from about 20 μm to about 100 μm, or from about 20 μm to about 90 μm, or from about 20 μm to about 80 μm, or from about 20 μm to about 70 μm, or from about 20 μm to about 60 μm, or from about 20 μm to about 50 μm, or from about 20 μm to about 40 μm, or from about 20 μm to about 30 μm, 30 μm to about 1500 μm, or from about 30 μm to about 1000 μm, or from about 30 μm to about 1500 μm, or from about 30 μm to about 900 μm, or from about 30 μm to about 800 μm, or from about 30 μm to about 700 μm, or from about 30 μm to about 600 μm, or from about 30 μm to about 500 μm, or from about 30 μm to about 400 μm, or from about 30 μm to about 300 μm, or from about 30 μm to about 200 µm, or from about 30 µm to about 100 µm, or from about 30 µm to about 90 µm, or from about 30 µm to about 80 µm, or from about 30 µm to about 70 µm, or from about 30 µm to about 60 µm, or from about 30 µm to about 50 µm, or from about 30 µm to about 40 µm, 40 µm to about 1500 µm, or from about 40 µm to about 1000 µm, or from about 40 µm to about 1500 µm, or from about 40 µm to about 900 µm, or from about 40 µm to about 800 µm, or from about 40 µm to about 700 µm, or from about 40 µm to about 600 µm, or from about 40 µm to about 500 µm, or from about 40 µm to about 400 µm, or from about 40 µm to about 300 µm, or from about 40 µm to about 200 µm, or from about 40 µm to about 100 µm, or from about 40 µm to about 90 µm, or from about 40 µm to about 80 µm, or from about 40 µm to about 70 µm, or from about 40 µm to about 60 µm, or from about 40 µm to about 50 µm, 50 µm to about 1500 µm, or from about 50 µm to about 1000 µm, or from about 50 µm to about 1500 µm, or from about 50 µm to about 900 µm, or from about 50 µm to about 800 µm, or from about 50 µm to about 700 µm, or from about 50 µm to about 600 µm, or from about 50 µm to about 500 µm, or from about 50 µm to about 400 µm, or from about 50 µm to about 300 µm, or from about 50 µm to about 200 µm, or from about 50 µm to about 100 µm, or from about 50 µm to about 90 µm, or from about 50 µm to about 80 µm, or from about 50 µm to about 70 µm, or from about 50 µm to about 60 µm, 60 µm to about 1500 µm, or from about 60 µm to about 1000 µm, or from about 60 µm to about 1500 µm, or from about 60 µm to about 900 µm, or from about 60 µm to about 800 µm, or from about 60 µm to about 700 µm, or from about 60 µm to about 600 µm, or from about 60 µm to about 500 µm, or from about 60 µm to about 400 µm, or from about 60 µm to about 300 µm, or from about 60 µm to about 200 µm, or from about 60 µm to about 100 µm, or from about 60 µm to about 90 µm, or from about 60 µm to about 80 µm, or from about 60 µm to about 70 µm, 70 µm to about 1500 µm, or from about 70 µm to about 1000 µm, or from about 70 µm to about 1500 µm, or from about 70 µm to about 900 µm, or from about 70 µm to about 800 µm, or from about 70 µm to about 700 µm, or from about 70 µm to about 600 µm, or from about 70 µm to about 500 µm, or from about 70 µm to about 400 µm, or from about 70 µm to about 300 µm, or from about 70 µm to about 200 µm, or from about 70 µm to about 100 µm, or from about 70 µm to about 90 µm, or from about 70 µm to about 80 µm, 80 µm to about 1500 µm, or from about 80 µm to about 1000 µm, or from about 80 µm to about 1500 µm, or from about 80 µm to about 900 µm, or from about 80 µm to about 800 µm, or from about 80 µm to about 700 µm, or from about 80 µm to about 600 µm, or from about 80 µm to about 500 µm, or from about 80 µm to about 400 µm, or from about 80 µm to about 300 µm, or from about 80 µm to about 200 µm, or from about 80 µm to about 100 µm, or from about 80 µm to about 90 µm, 90 µm to about 1500 µm, or from about 90 µm to about 1000 µm, or from about 90 µm to about 1500 µm, or from about 90 µm to about 900 µm, or from about 90 µm to about 800 µm, or from about 90 µm to about 700 µm, or from about 90 µm to about 600 µm, or from about 90 µm to about 500 µm, or from about 90 µm to about 400 µm, or from about 90 µm to about 300 µm, or from about 90 µm to about 200 µm, or from about 90 µm to about 100 µm, 100 µm to about 1500 µm, or from about 100 µm to about 1000 µm, or from about 100 µm to about 1500 µm, or from about 100 µm to about 900 µm, or from about 100 µm to about 800 µm, or from about 100 µm to about 700 µm, or from about 100 µm to about 600 µm, or from about 100 µm to about 500 µm, or from about 100 µm to about 400 µm, or from about 100 µm to about 300 µm, or from about 100 µm to about 200 µm, 200 µm to about 1500 µm, or from about 200 µm to about 1000 µm, or from about 200 µm to about 1500 µm, or from about 200 µm to about 900 µm, or from about 200 µm to about 800 µm, or from about 200 µm to about 700 µm, or from about 200 µm to about 600 µm, or from about 200 µm to about 500 µm, or from about 200 µm to about 400 µm, or from about 200 µm to about 300 µm, 300 µm to about 1500 µm, or from about 300 µm to about 1000 µm, or from about 300 µm to about 1500 µm, or from about 300 µm to about 900 µm, or from about 300 µm to about 800 µm, or from about 300 µm to about 700 µm, or from about 300 µm to about 600 µm, or from about 300 µm to about 500 µm, or from about 300 µm to about 400 µm, 400 µm to about 1500 µm, or from about 400 µm to about 1000 µm, or from about 400 µm to about 1500 µm, or from about 400 µm to about 900 µm, or from about 400 µm to about 800 µm, or from about 400 µm to about 700 µm, or from about 400 µm to about 600 µm, or from about 400 µm to about 500 µm, 500 µm to about 1500 µm, or from about 500 µm to about 1000 µm, or from about 500 µm to about 1500 µm, or from about 500 µm to about 900 µm, or from about 500 µm to about 800 µm, or from about 500 µm to about 700 µm, or from about 500 µm to about 600 µm, 600 µm to about 1500 µm, or from about 600 µm to about 1000 µm, or from about 600 µm to about 1500 µm, or from about 600 µm to about 900 µm, or from about 600 µm to about 800 µm, or from about 600 µm to about 700 µm, 700 µm to about 1500 µm, or from about 700 µm to about 1000 µm, or from about 700 µm to about 1500 µm, or from about 700 µm to about 900 µm, or from about 700 µm to about 800 µm, 800 µm to about 1500 µm, or from about 800 µm to about 1000 µm, or from about 800 µm to about 1500 µm, or from about 800 µm to about 900 µm, 900 µm to about 1500 µm, or from about 900 µm to about 1000 µm, 1000 µm to about 1500 µm.

The thickness of the shell varies in the range of 50 nm to 500 µm. The thickness of the functional surface layer using the post-functionalization method is of several nanometers (1-10 nm). The density of the microcapsules can be as low as 0.001 g/cm$^3$, approximately 1/1000 of the density of most plastics, composites, rubbers, and textiles products. The density of the microcapsule ranges from about as 0.001 g/cm$^3$ to about 1.0 g/cm$^3$, or from about 0.005 g/cm$^3$ to about 1.0 g/cm$^3$, or from about 0.01 g/cm$^3$ to about 1.0 g/cm$^3$, or from about 0.02 g/cm$^3$ to about 1.0 g/cm$^3$, or from about 0.03 g/cm$^3$ to about 1.0 g/cm$^3$, or from about 0.04 g/cm$^3$ to about 1.0 g/cm$^3$, or from about 0.05 g/cm$^3$ to about 1.0 g/cm$^3$, or from about 0.06 g/cm$^3$ to about 1.0 g/cm$^3$, or from about 0.07 g/cm$^3$ to about 1.0 g/cm$^3$, or from about 0.08 g/cm$^3$ to about 1.0 g/cm$^3$, or from about 0.09 g/cm$^3$ to about 1.0 g/cm$^3$, or from about 0.1 g/cm$^3$ to about 1.0 g/cm$^3$, or from about 0.2 g/cm$^3$ to about 1.0 g/cm$^3$, or from about 0.3 g/cm$^3$ to about 1.0 g/cm$^3$, or from about 0.4 g/cm$^3$ to about 1.0 g/cm$^3$, or from about 0.5 g/cm$^3$ to about 1.0 g/cm$^3$, or from about 0.6 g/cm$^3$ to about 1.0 g/cm$^3$, or from about 0.7 g/cm$^3$ to about 1.0 g/cm$^3$, or from about 0.8 g/cm$^3$ to about 1.0 g/cm$^3$, or from about 0.9 g/cm$^3$ to about 1.0 g/cm$^3$, or from about 0.005 g/cm$^3$ to about 1.0 g/cm$^3$, or from about as 0.001 g/cm$^3$ to about 0.9 g/cm$^3$, or from about 0.005 g/cm$^3$ to about 0.9 g/cm$^3$, or from about 0.01 g/cm$^3$ to about 0.9 g/cm$^3$, or from about 0.02 g/cm$^3$ to about 0.9 g/cm$^3$, or from about 0.03 g/cm$^3$ to about 0.9 g/cm$^3$, or from about 0.04 g/cm$^3$ to about 0.9 g/cm$^3$, or from about 0.05 g/cm$^3$ to about 0.9 g/cm$^3$, or from about 0.06 g/cm$^3$ to about 0.9 g/cm$^3$, or from about 0.07 g/cm$^3$ to about 0.9 g/cm$^3$, or from about 0.08 g/cm$^3$ to about 0.9 g/cm$^3$, or from about 0.09 g/cm$^3$ to about 0.9 g/cm$^3$, or from about 0.1 g/cm$^3$ to about 0.9 g/cm$^3$, or from about 0.2 g/cm$^3$ to about 0.9 g/cm$^3$, or from about 0.3 g/cm$^3$ to about 0.9 g/cm$^3$, or from about 0.4 g/cm$^3$ to about 0.9 g/cm$^3$, or from about 0.5 g/cm$^3$ to about 0.9 g/cm$^3$, or from about 0.6 g/cm$^3$ to about 0.9 g/cm$^3$, or from about 0.7 g/cm$^3$ to about 0.9 g/cm$^3$, or from about 0.8 g/cm³ to about 0.9 g/cm³, or from about as 0.001 g/cm³ to about 0.8 g/cm³, or from about 0.005 g/cm³ to about 0.8 g/cm³, or from about 0.01 g/cm³ to about 0.8 g/cm³, or from about 0.02 g/cm³ to about 0.8 g/cm³, or from about 0.03 g/cm³ to about 0.8 g/cm³, or from about 0.04 g/cm³ to about 0.8 g/cm³, or from about 0.05 g/cm³ to about 0.8 g/cm³, or from about 0.06 g/cm³ to about 0.8 g/cm³, or from about 0.07 g/cm³ to about 0.8 g/cm³, or from about 0.08 g/cm³ to about 0.8 g/cm³, or from about 0.09 g/cm³ to about 0.8 g/cm³, or from about 0.1 g/cm³ to about 0.8 g/cm³, or from about 0.2 g/cm³ to about 0.8 g/cm³, or from about 0.3 g/cm³ to about 0.8 g/cm³, or from about 0.4 g/cm³ to about 0.8 g/cm³, or from about 0.5 g/cm³ to about 0.8 g/cm³, or from about 0.6 g/cm³ to about 0.8 g/cm³, or from about 0.7 g/cm³ to about 0.8 g/cm³, or from about as 0.001 g/cm³ to about 0.7 g/cm³, or from about 0.005 g/cm³ to about 0.7 g/cm³, or from about 0.01 g/cm³ to about 0.8 g/cm³, or from about 0.02 g/cm³ to about 0.7 g/cm³, or from about 0.03 g/cm³ to about 0.7 g/cm³, or from about 0.04 g/cm³ to about 0.7 g/cm³, or from about 0.05 g/cm³ to about 0.7 g/cm³, or from about 0.06 g/cm³ to about 0.7 g/cm³, or from about 0.07 g/cm³ to about 0.7 g/cm³, or from about 0.08 g/cm³ to about 0.7 g/cm³, or from about 0.09 g/cm³ to about 0.7 g/cm³, or from about 0.1 g/cm³ to about 0.7 g/cm³, or from about 0.2 g/cm³ to about 0.7 g/cm³, or from about 0.3 g/cm³ to about 0.7 g/cm³, or from about 0.4 g/cm³ to about 0.7 g/cm³, or from about 0.5 g/cm³ to about 0.7 g/cm³, or from about 0.6 g/cm³ to about 0.7 g/cm³, or from about as 0.001 g/cm³ to about 0.6 g/cm³, or from about 0.005 g/cm³ to about 0.6 g/cm³, or from about 0.01 g/cm³ to about 0.8 g/cm³, or from about 0.02 g/cm³ to about 0.6 g/cm³, or from about 0.03 g/cm³ to about 0.6 g/cm³, or from about 0.04 g/cm³ to about 0.6 g/cm³, or from about 0.05 g/cm³ to about 0.6 g/cm³, or from about 0.06 g/cm³ to about 0.6 g/cm³, or from about 0.07 g/cm³ to about 0.6 g/cm³, or from about 0.08 g/cm³ to about 0.6 g/cm³, or from about 0.09 g/cm³ to about 0.6 g/cm³, or from about 0.1 g/cm³ to about 0.6 g/cm³, or from about 0.2 g/cm³ to about 0.6 g/cm³, or from about 0.3 g/cm³ to about 0.6 g/cm³, or from about 0.4 g/cm³ to about 0.6 g/cm³, or from about 0.5 g/cm³ to about 0.6 g/cm³, or from about as 0.001 g/cm³ to about 0.5 g/cm³, or from about 0.005 g/cm³ to about 0.5 g/cm³, or from about 0.01 g/cm³ to about 0.8 g/cm³, or from about 0.02 g/cm³ to about 0.5 g/cm³, or from about 0.03 g/cm³ to about 0.5 g/cm³, or from about 0.04 g/cm³ to about 0.5 g/cm³, or from about 0.05 g/cm³ to about 0.5 g/cm³, or from about 0.06 g/cm³ to about 0.5 g/cm³, or from about 0.07 g/cm³ to about 0.5 g/cm³, or from about 0.08 g/cm³ to about 0.5 g/cm³, or from about 0.09 g/cm³ to about 0.5 g/cm³, or from about 0.1 g/cm³ to about 0.5 g/cm³, or from about 0.2 g/cm³ to about 0.5 g/cm³, or from about 0.3 g/cm³ to about 0.5 g/cm³, or from about 0.4 g/cm³ to about 0.5 g/cm³, or from about as 0.001 g/cm³ to about 0.4 g/cm³, or from about 0.005 g/cm³ to about 0.4 g/cm³, or from about 0.01 g/cm³ to about 0.8 g/cm³, or from about 0.02 g/cm³ to about 0.4 g/cm³, or from about 0.03 g/cm³ to about 0.4 g/cm³, or from about 0.04 g/cm³ to about 0.4 g/cm³, or from about 0.05 g/cm³ to about 0.4 g/cm³, or from about 0.06 g/cm³ to about 0.4 g/cm³, or from about 0.07 g/cm³ to about 0.4 g/cm³, or from about 0.08 g/cm³ to about 0.4 g/cm³, or from about 0.09 g/cm³ to about 0.4 g/cm³, or from about 0.1 g/cm³ to about 0.4 g/cm³, or from about 0.2 g/cm³ to about 0.4 g/cm³, or from about 0.3 g/cm³ to about 0.4 g/cm³, or from about as 0.001 g/cm³ to about 0.3 g/cm³, or from about 0.005 g/cm³ to about 0.3 g/cm³, or from about 0.01 g/cm³ to about 0.8 g/cm³, or from about 0.02 g/cm³ to about 0.3 g/cm³, or from about 0.03 g/cm³ to about 0.3 g/cm³, or from about 0.04 g/cm³ to about 0.3 g/cm³, or from about 0.05 g/cm³ to about 0.3 g/cm³, or from about 0.06 g/cm³ to about 0.3 g/cm³, or from about 0.07 g/cm³ to about 0.3 g/cm³, or from about 0.08 g/cm³ to about 0.3 g/cm³, or from about 0.09 g/cm³ to about 0.3 g/cm³, or from about 0.1 g/cm³ to about 0.3 g/cm³, or from about 0.2 g/cm³ to about 0.3 g/cm³, or from about as 0.001 g/cm³ to about 0.2 g/cm³, or from about 0.005 g/cm³ to about 0.2 g/cm³, or from about 0.01 g/cm³ to about 0.8 g/cm³, or from about 0.02 g/cm³ to about 0.2 g/cm³, or from about 0.03 g/cm³ to about 0.2 g/cm³, or from about 0.04 g/cm³ to about 0.2 g/cm³, or from about 0.05 g/cm³ to about 0.2 g/cm³, or from about 0.06 g/cm³ to about 0.2 g/cm³, or from about 0.07 g/cm³ to about 0.2 g/cm³, or from about 0.08 g/cm³ to about 0.2 g/cm³, or from about 0.09 g/cm³ to about 0.2 g/cm³, or from about 0.1 g/cm³ to about 0.2 g/cm³, or from about as 0.001 g/cm³ to about 0.1 g/cm³, or from about 0.005 g/cm³ to about 0.1 g/cm³, or from about 0.01 g/cm³ to about 0.8 g/cm³, or from about 0.02 g/cm³ to about 0.1 g/cm³, or from about 0.03 g/cm³ to about 0.1 g/cm³, or from about 0.04 g/cm³ to about 0.1 g/cm³, or from about 0.05 g/cm³ to about 0.1 g/cm³, or from about 0.06 g/cm³ to about 0.1 g/cm³, or from about 0.07 g/cm³ to about 0.1 g/cm³, or from about 0.08 g/cm³ to about 0.1 g/cm³, or from about 0.09 g/cm³ to about 0.1 g/cm³, or from about as 0.001 g/cm³ to about 0.09 g/cm³, or from about 0.005 g/cm³ to about 0.09 g/cm³, or from about 0.01 g/cm³ to about 0.8 g/cm³, or from about 0.02 g/cm³ to about 0.09 g/cm³, or from about 0.03 g/cm³ to about 0.09 g/cm³, or from about 0.04 g/cm³ to about 0.09 g/cm³, or from about 0.05 g/cm³ to about 0.09 g/cm³, or from about 0.06 g/cm³ to about 0.09 g/cm³, or from about 0.07 g/cm³ to about 0.09 g/cm³, or from about 0.08 g/cm³ to about 0.09 g/cm³, or from about as 0.001 g/cm³ to about 0.08 g/cm³, or from about 0.005 g/cm³ to about 0.08 g/cm³, or from about 0.01 g/cm³ to about 0.8 g/cm³, or from about 0.02 g/cm³ to about 0.08 g/cm³, or from about 0.03 g/cm³ to about 0.08 g/cm³, or from about 0.04 g/cm³ to about 0.08 g/cm³, or from about 0.05 g/cm³ to about 0.08 g/cm³, or from about 0.06 g/cm³ to about 0.08 g/cm³, or from about 0.07 g/cm³ to about 0.08 g/cm³, or from about as 0.001 g/cm³ to about 0.07 g/cm³, or from about 0.005 g/cm³ to about 0.07 g/cm³, or from about 0.01 g/cm³ to about 0.8 g/cm³, or from about 0.02 g/cm³ to about 0.07 g/cm³, or from about 0.03 g/cm³ to about 0.07 g/cm³, or from about 0.04 g/cm³ to about 0.07 g/cm³, or from about 0.05 g/cm³ to about 0.07 g/cm³, or from about 0.06 g/cm³ to about 0.07 g/cm³, or from about as 0.001 g/cm³ to about 0.06 g/cm³, or from about 0.005 g/cm³ to about 0.06 g/cm³, or from about 0.01 g/cm³ to about 0.8 g/cm³, or from about 0.02 g/cm³ to about 0.06 g/cm³, or from about 0.03 g/cm³ to about 0.06 g/cm³, or from about 0.04 g/cm³ to about 0.06 g/cm³, or from about 0.05 g/cm³ to about 0.06 g/cm³, or from about as 0.001 g/cm³ to about 0.05 g/cm³, or from about 0.005 g/cm³ to about 0.05 g/cm³, or from about 0.01 g/cm³ to about 0.8 g/cm³, or from about 0.02 g/cm³ to about 0.05 g/cm³, or from about 0.03 g/cm³ to about 0.05 g/cm³, or from about 0.04 g/cm³ to about 0.05 g/cm³, or from about as 0.001 g/cm³ to about 0.04 g/cm³, or from about 0.005 g/cm³ to about 0.04 g/cm³, or from about 0.01 g/cm³ to about 0.8 g/cm³, or from about 0.02 g/cm³ to about 0.04 g/cm³, or from about 0.03 g/cm³ to about 0.04 g/cm³, or from about as 0.001 g/cm³ to about 0.03 g/cm³, or from about 0.005 g/cm³ to about 0.03 g/cm³, or from about 0.01 g/cm³ to about 0.03 g/cm³, or from about 0.02 g/cm³ to about 0.03 g/cm³, or from about as 0.001 g/cm³ to about 0.02 g/cm³, or from about 0.005 g/cm³ to about 0.02 g/cm³, or from about 0.01 g/cm³ to about 0.02 g/cm³, or from about as 0.001 g/cm³ to about 0.01 g/cm³, or from about 0.005 g/cm³ to about 0.01 g/cm³, or from about as 0.001 g/cm³ to about 0.005 g/cm³.

According to an embodiment, the shell comprises from about 0% to about 70% Q3 configuration (i.e. the silicon atoms form siloxane bonds with tree neighbors), and from about 30% to about 100% Q4 configuration (the silicon atoms form siloxane bridges with 4 neighbors). According to another embodiment, the shell comprises from about 40% Q3 configuration and from about 60% 04 configuration. According to another embodiment, the shell comprises less than about 10% Q3 configuration and more than about 90% Q4 configuration. According to a preferred embodiment the shell comprises 100% 04 configuration.

According to another embodiment, the shell may comprise from about 0% to about 60% T2 form silica and from about 40% to about 100% T3 form silica.

According to another embodiment, the shell may comprise combinations of T and Q configurations thereof.

Referring now to the drawings, and more particularly to FIG. 1, which shows a NMR spectrum of a microcapsule according to the present invention, having about 45% Q3 and about 55% Q4 before thermal annealing and about 0% Q3 and 100% Q4 after thermal annealing.

According to an embodiment, the shell of the microcapsule of the present invention may comprise a plurality of pores, having diameters of from about 0.5 nm to about 100 nm.

The exterior surface layer of the proprietary silica microcapsules comprises functional groups such as hydroxyl groups, amino groups, benzylamino groups, chloropropyl groups, disulfide groups, epoxy groups, mercapto groups, methacrylate groups, and vinyl groups. Also, the surface can be further modified by other organofunctional groups. According to another embodiment, the microcapsule may further comprise a functionalized surface layer. According to an embodiment, the functionalized surface layer may comprise a thickness of about several nanometers. The functionalized surface layer may comprise for example one or more organosilanes compounds, as well as other compounds. For example, the organosilane may be without limitations 3-aminopropyltriethoxysilane, vinyltriacetoxy silane, vinyltrimethoxysilane, 3-glycidoxypropyltrimethoxysilane, 3-methacryloxypropyltrimethoxysilane, 3-chloropropyltriethoxysilane, bis-(triethoxysilylpropyl)tetrasulfane, methyltriethoxysilane, n-octyltriethoxysilane, phenyltrimethoxysilane, methacryloyloxypropyltrimethoxysilane, phenyltriethoxysilane, phenyltrimethoxysilane, glycidoxypropoxyltrimethoxysilane, glycidoxypropyltriethoxysilane, mercaptopropyltriethoxysilane, mercaptopropyltrimethoxysilane, aminopropyltrimethoxysilane, 3-aminopropyltriethoxysilane, 3-(2-aminoethylamino)propyltrimethoxysilane, 3-[2-(2-aminoethylamino)ethylamino]propyltrimethoxysilane, [2(cyclohexenyl)ethyl]triethoxysilane, vinyltrimethoxysilane, vinyltriethoxysilane or a mixture of any two or more of the above and combinations thereof. Non limiting examples of functionalizing groups include amino groups, epoxy groups, vinyl groups, methacrylate groups, benzylamino groups, chloropropyl groups, disulfide groups, epoxy groups, mercapto groups and combinations thereof. The functional groups allow the microcapsules of the present invention to gain affinity or adhesion to the matrix of plastics, composites, rubbers and textiles materials and products for examples. According to another embodiment, the functional groups may also serve to crosslink other molecules to the exterior surface of the microcapsule of the present invention.

The microcapsules, as a density-reducing additive, are usually provided in powder. The melting point for this additive is as high as 1600-1725° C. This additive is also very environment-friendly.

According to another embodiment, the microcapsule of the present invention may further comprise a conductive layer surrounding the exterior surface of the microcapsule. According to an embodiment, the conductive layer is a metallic layer or a conductive polymer layer. Non-limiting examples of conductive polymer include polypyrroles, polythiophenes, polyanilines, and the likes. According to another embodiment, the metallic layer is a layer of silver, copper, gold, or aluminum, for example.

According to another embodiment, the microcapsules of the present invention may further comprise an active agent. Examples of suitable active agent include without limitations a catalyst for monomers polymerization (used for example in resins: epoxy, phenolic, polyester or vinylic resins). Non-limiting examples include curing agents for epoxy resins: aliphatic amines [Diethylenetriamine (DTA), Diethylaminopropylamine (DEAPA)], aromatic amines [Diaminodiphenylmethane (DDM), Metaphenylene diamine (MPDA)], tertiary and secondary amines (N,N-dimethylpiperidine, Benzyldimethylamine), modified amines (Ketoimine), polyamide resins, imidazoles (2-methylimidazole, 1-cyanoethyl-2-undecylimidazolium trimellitate), anhydrides (Maleic anhydride, Ethylene glycol bistrimellitate, Dodecenyl succinic anhydride). Catalysts for polyester and vinyl ester resins: Methyl Ketone Peroxide, 2-Butanone peroxide, cumyl hydroperoxide, acetyl acetone peroxide, tertiary-butyl peroxybenzoate, tertiary-amyl peroxybenzoate, tertiary-butyl peroxybenzoate. Initiators for phenolic resins: acid-catalysed (e.g. sulphonic acid), base-catalysed (e.g. Hexamethylenetetramine).

Other examples of suitable active agent include without limitations a stabilizer chemical such as antioxidants used in polymers e.g. phenolic antioxydants (Butylated hydroxytoluene (BHT), α-tocopherol, tocopheryl acetate), organophosphates (Tris(2,4-di-tert-butylphenyl)phosphite, trisnonylphenyl phosphite), thioesters (Dilauryl thiodipropionate, Distearyl thiodipropionate,) and the likes), light stabilisers for polymers: Hindered Amine Light Stabilizers HALS (e.g. 2,2,6,6-tetramethyl-4-piperidyl)sebacate), benzotriazoles, benzophenones, Other examples of suitable active agent include without limitations a fire retardant chemical, such as tetrabromobisphenol-A, decabromodiphenylethane, dibromoneopentylglycol, a colorant, such as carbon black, molybdate orange, chrome oxide green, anthanthrone, anthraquinone, benzimidazole, quinacridone, a pharmaceutically active drug, an a protein, an enzyme, other biological molecule (antibodies, catalyst, reagents, DNA, RNA, vitamins), cosmetic oils, fragrances, perfume, food colorant, food additives, humidifier, explosive, phase change material (PCM), insecticide, herbicide, fungicide, and combinations thereof. According to an embodiment, the active agent may be cross-linked to the functionalized surface layer, to the exterior surface, or both. According to another embodiment, the active agent may be encapsulated in the microcapsule.

The microcapsules of the present invention may be introduced into plastics, composites, rubbers, or textiles materials or products in their processing stages. The microcapsules can be dispersed into the final products throughout or in part. The density of the final products containing the described microcapsules can be lowered at little or no cost to their performance due to the extreme low density of the additive itself and the affinity between the additive and the matrix.

With regard to the low density feature and the modifiable functional surface layer, the proprietary silica microcapsules are excellent weight-reducing fillers to many polymer resins and polymer blends, including low, medium and high density polyethylene (PE), polypropylene (PP), polystyrene (PS), polycarbonate (PC), polyurethane (PU), polybutadiene (PB), polyethylene terephthalate (PET), polybutylene terephthalate (PBT), polyoxymethylene (POM), polymethacrylate (PMA), poly(methyl methacrylate) (PMMA), nylon, poly(vinyl chloride) (PVC), Acrylonitrile butadiene styrene (ABS), polylactide (PLA), polyvinylidene chloride, and polyether ether ketone (PEK). The hardness of silica materials ensures that the majority of the microcapsules can survive even at a high shearing flow.

The hydroxyl groups in the exterior surface layer of the proprietary silica microcapsules exhibit good affinity to many polymers containing proton acceptors such as poly(acid acrylic) and poly(vinyl alcohol), and thus the microcapsules can be used directly as reinforcement. Also, the exterior surface layer can be further modified by other organofunctional groups to form a functionalized surface layer and thus allow coupling effects to many other plastics. When the functionalized surface layer is covered by amino groups, they can be coupled with epoxies, phenolics, melamines, nylons, PVC, acrylics, polyolefins, polyurethanes, nitrile rubbers, and blends thereof, and nitrile rubbers. Epoxy functionalized silica microcapsules can be coupled with epoxies, polyurethanes, acrylics, and polysulfides, Vinyl covered silica microcapsules can be coupled with polyolefins, EPDM rubber, and styrene-butadiene (SBR. A methacrylate modified surface shows excellent coupling effect to unsaturated polyesters, acrylics, and polyolefins Chloropropyl covered silica microcapsules can be coupled with polyurethanes, epoxies, nylons, phenolics, polyolefins. Mercapto and disulfide functionalized silica microcapsules show excellent coupling effect to organic rubbers. Benzylamino and vinyl-benzyl-amino modified surfaces can be coupled with all polymer types.

According to another embodiment, anti-blocking additives are commonly seen in the formulation of plastic films to create a micro-rough surface that reduces the adhesion between the film layers. Silica gel, structurally composed of an interconnected random array of ultimate, polymerized silicate particles, is a major anti-blocking additive in plastics because of its fundamental properties. The surface of the microcapsules can be controlled from very smooth to very rough, which also depends on the parameters of the proprietary process. In this case, these microcapsules are also used as anti-blocking additives to the plastic products, such as PP, PE, and PET.

According to another embodiment, the native microcapsules of the present invention are covered by an exterior surface composed of polar hydroxyl groups, and they are thus ready to decrease the contact angle between water and themselves. In view of their ability to decrease the surface tension of water, microcapsules of the present invention may be used as antifogging additives in plastics.

According to another embodiment, the fundamental property of amourphous silica itself, its high melting point (1600-1725° C.), and make microcapsules of the present invention good heat stabilizers, fire resistants and flame retardants. In addition, some organic flame retardant compounds, such as chlorendic anhydride, decabromobiphenyl, octabromodiphenyloxide, upon encapsulated into the interior of the silica microcapsules, provide better flame retardant performance.

According to another embodiment, the microcapsules of the present invention can contain microencapsulated phase change materials for thermal energy storage, wherein said phase material is selected from the group consisting of n-octacosane, n-Heptacosane, n-tricosane, n-eicosane, n-octadecane, n-pentadecane, n-tridecane, etc.

According to another embodiment, the proprietary silica microcapsules can also be used as nucleating agents to some semi-crystalline polymers, such as PE, PP, PET (polyethylene terephtalate), and polyamides (PA). The size of the microcapsules can be controlled to match the size of the crystal of these polymers. In addition, the melting point of silica is far higher than that of all the semi-crystalline polymers. All properties these make them very useful nucleating agents.

According to another embodiment, the hydroxyl groups in the exterior surface of the native microcapsules of the present invention show some weak base property. This allows them to neutralize the acidic products during polymerization reactions, as well as allow the use of Ziegler-Natta catalysts. This property thus allows the native microcapsules to act as acid scavengers in plastics, such as linear low-density PE, high-density PE, and PP.

According to another embodiment, the interior of the silica microcapsules can be filled with pigments or dyes. In this case, the silica microcapsules can be used as colorants or fluorescent whitening agents." Non-limiting examples pigments include but are not limited to carbon black, molybdate orange, chrome oxide green. Non-limiting examples of dyes include anthanthrone, anthraquinone, benzimidazole, and quinacridone.

According to another embodiment, silica hollow microcapsules can be used as thermal, electrical and sound insulators for numerous materials, including polymers.

Process for the Preparation of Microcapsules

According to the second embodiment there is disclosed a process for the preparation of a microcapsule which comprises step a)
a) contacting with an acidic or alkali catalyst an emulsion formed between a water phase comprising water, an alcohol and a surfactant, and an oil phase comprising a silica precursor and a hydrophobic solvent or an oil, for a time sufficient and at a temperature sufficient obtain a formed microcapsule in a liquid phase.

The process of the present invention allows the preparation of silica microcapsules on a large scale. According to an embodiment, one goal of this process is to reduce the cost by utilizing commercially available oil, such as vegetable oil as the template of the oil phase in an emulsion reaction.

The process of the present invention is based on the sol-gel transition of the oil phase in an oil-in-water (O/W) or water-in-oil (W/O) emulsion and essentially composed of a few steps to fabricate microcapsules in a bath fashion or a continuous way: emulsion, decantation and drying.

In the process of the present invention, an oil-in-water (O/W) emulsion is usually preferred than the reverse water-in-oil emulsion due to the cost. In the emulsion system, the oil phase comprises silica precursor and vegetable oil or a hydrophobic solvent. The silica precursor can be one or more silanes having 1, 2, 3 or 4 hydrolysable groups per molecule. The hydrolysable groups can be methoxy, ethoxy, propoxy, isopropoxy, phenoxy or some other hydrolysable groups. The silica precursor can be for example tetramethoxysilane (TMOS), tetraethoxysilane (TEOS), tetrapropoxysilane (TPOS) or a functional trimethoxy, triethoxy or tripropoxysilane, such as aminopropylsilane, aminoethylaminopropylsilane, vinyltrmethoxysilane, 3-chloropropyltriethoxysilane, 3-glycidoxypropyltrimethoxysilane, or a combination thereof.

According to another embodiment, the vegetable oil can be sourced from palm, soybean, rapeseed, sunflower seed, peanut, cottonseed, palm kernel, coconut, corn, grape seed, hazelnut, linseed, rice bran, safflower, sesame and olive. According to another embodiment, the hydrophobic solvent can be heptane, hexane, pentane, cyclopentane, toluene, decalin, benzene, carbon tetrachloride, cyclohexane, 1,4 dioxane and chloroform.

In detail, a silica precursor, typically tetraethyl orthosilicate (TEOS) or tetramethyl orthosilicate (TMOS), is dissolved in vegetable oil or a hydrophobic solvent, with a weight ratio of the former to the later ranging from about a 4:1 to about a 1:10 (silica precursor:oil or solvent ratio), to make a homogeneous solution after stirring.

According to an embodiment, for an O/W emulsion, the oil phase containing the silica precursor, the vegetable oil or the hydrophobic solvent is added under vigorous stirring into a reactor containing an excess of the water phase, which comprises water, an alcohol (such as ethanol, methanol, propanol, butanol, glycerol), a catalyst for sol-gel reaction (an acid or an alkali) and one or more surfactants. The percentage of the silica precursor in the oil phase ranges from 10 to 80% (wt/wt), depending on the required properties of the microcapsules. Alcohol is added in the water phase with a proportion from 1 to 20 wt % (wt/wt). Deionized water is used in the process of the invention, which occupies 80 to 95 wt % (wt/wt) of the total water phase.

For a W/O emulsion, the process conditions are equivalent, except that the emulsion is obtained by adding the water phase to an excess of vegetable oil or hydrophobic solvent, followed by a slow incorporation of the silica precursor.

According to an embodiment, many surfactants can be used in the process of the present invention to yield a stable emulsion with desired oil drop sizes, depending on the required HLB value of the surfactant. Non limiting examples of suitable surfactants include but are not limited to surfactants with HLB between 1 and 10 such as sorbitan trioleate (Span 85), sorbitan tristearate (Span 65) or sorbitan sesquioleate, sorbitan monolaurate (Span 20), PEO/PPO copolymers, glycerol monooleate, sorbitan monooleate (SPAN80), or surfactants with HLB between 10 and 20 such as: polyoxyethylene derivative of sorbitan ester (Tween 20, Tween 61, Tween80), polyoxyethylene fatty ether (Brij35, Brij93), nonylphenoxypolyethoxyethanol (NP-6, NP-9), octylphenoxypolyethoxyethanol (TritonX-100, TritonX-114), cetyltrimethylammonium bromide (CTAB), and combinations thereof.

According to an embodiment, the concentration of surfactant in the mixture usually may fall into the range of 0.05 mM to 15 mM, and preferably 2.5 mM. According to another embodiment, the weight concentration of the surfactant in the mixture usually falls into the range of 0.1 wt % to 4 wt %, and is preferably 0.5 wt %.

The emulsification is performed using high shear forces (stirring speed from 300 to 10000 rpm on a Caframo Universal model BDC 3030 high torque overhead stirrer). The formation of the well dispersed emulsion is carried out for about 2 to about 60 minutes, or preferably for about 2 to 20 minutes. Usually 2 to 20 minutes of high speed stirring is enough to make a well dispersed, stable emulsion. The catalyst of the sol-gel reaction may be acid or basic. The pH of the emulsion can be between about 1 and 12, or may be outside the range of 1-12. The pH may be adjusted to the desired value using an acid, for example hydrochloric, sulfuric, phosphoric, nitric, or some other acid, or using a base, for example sodium hydroxide, potassium hydroxide or ammonia. The sol-gel reaction can be carried out at room temperature (about 20° C.) or by raising slightly the temperature to about 50° C., when the reaction is carried out for about 30 minutes to 18 hours.

According to another embodiment, the process of the present invention may comprise step b) after step a):
b) washing the formed microcapsule to remove the acidic or alkali catalyst, the surfactant and the oil, to obtain washed microcapsules.

According to an embodiment, the products are washed with water to remove the catalyst and most of the surfactants, and then washed with a hydrophobic solvent (e.g. hexane, heptanes, or diethyl ether) to remove the remaining silica precursor, and the remaining surfactant. According to an embodiment, when vegetable oil is used, this washing step may also wash away the oil and replace it for example with a hydrophobic solvent.

According to another embodiment, the process of the present invention may comprise step c') after step b),
c) separating the formed microcapsule from the liquid phase in which they were formed.

According to an embodiment, they are firstly separated by a separatory apparatus and then filtered to remove most of the liquid phase. Decantation is a preferred method of separation since the oil drops are lighter than water. Centrifugation is the most preferred method of separation.

According to another embodiment, the process of the present invention may comprise step d) after step c):
d) drying the washed microcapsules to obtain dried microcapsules.

According to an embodiment, the products are dried into white fine powders. The supernatant cream or milk-like liquid may be transferred to a drying apparatus to remove the extra water and organic solvent or to calcine the vegetable oil (temperature from 200° C. to 800° C.). Spray drying and lyophilisation are preferred drying methods. According to an embodiment, spray drying is the most preferred drying method. The final silica microcapsules are white powders.

According to another embodiment, in some cases, the process of the present invention may comprise step e) after step d):
e) thermal annealing of said dried microcapsules at 700° C. to less than about 1100° C.

According to another embodiment, the thermal annealing may be preferably performed at about 800° C. to about 1000° C. Thermal annealing converts the Q3 configuration to Q4 configuration, or the T2 configuration to T3 configuration, which improve the mechanical properties of the microcapsule by increasing their strength for example.

According to another embodiment, after the drying stage (step d), a functional trimethoxy, triethoxy or tripropoxysilane, such as aminopropylsilane, aminoethylaminopropylsilane, vinyltrmethoxysilane, 3-chloropropyltriethoxysilane, 3-glycidoxypropyltrimethoxysilane, methacryloyloxypropyltrimethoxysilane, phenyltriethoxysilane, phenyltrimethoxysilane, mercaptopropyltrimethoxysilane, etc., or a combination thereof can be used to functionalize the microcapsules. The post-functionalization can be performed in solution under inert atmosphere (e.g. nitrogen, argon and other atmospheres) by dispersing the dried silica microcapsules in a dried organic solvent (e.g. dichloromethane, tetrahydrofuran and ethyl acetate) in the presence of one or more organoreactive silanes and an organic acid (e.g. carboxylic acids) or an organic base (e.g. amines) as catalyst for sol-gel reaction. The reaction can be performed at temperatures ranging from 20° C. to 50° C. for a time sufficient to effect functionalization. In the following steps, the obtained functionalized microcapsules are separated from the liquid phase by filtration or centrifugation and dried at temperatures ranging from 30° C. to 120° C., under vacuum or at a normal pressure or using for example a spray drying system.

According to another embodiment, the post-functionalization can also be performed in solid state, in the presence of organosilane vapors, using for example a column equipped with heating and vacuum equipments, a fluid bed and spray dryers, etc., for a time sufficient to effect functionalization.

According to another embodiment, post-functionalization in solid state is the most preferred method.

According to another embodiment, the functionalization step can be performed during the emulsion by directly incorporating an organosilane in the oil phase, among the silica precursors.

According to an embodiment, the waste produced during the purification stage of this process can be easily recycled and thus become environmentally friendly. First, the waste is separated in a separatory apparatus into a water phase and an oil phase. The water phase containing water, alcohol, acid or alkali and some surfactants can be reused after a preliminary analysis of the different constituents. The oil phase containing hydrophobic solvent (heptanes, hexane, decalin or toluene) can be separated from unreacted silica precursor and other impurities by distillation. The vegetable oil can be reused after being analysed (traces of surfactants and silica precursors). In such a case, this process can be easily commercialized to a large scale in an ecologically-friendly fashion.

The present invention dedicatedly combined the advantages of both emulsion techniques and the sol-gel technique to deliver a low cost solution to produce The surface functionalization can be accomplished just by exposing the silica microcapsules to the vapour of the surface-coating chemicals. Functional trimethoxy, triethoxy and tripropoxysilanes such as aminopropyltriethoxysilane, vinyltriacetoxy silane, vinyltrimethoxysilane, 3-glycidoxypropyltrimethoxysilane, 3-methacryloxypropyltrimethoxysilane, 3-chloropropyltriethoxysilane, bis-(triethoxysilylpropyl)tetrasulfane, methyltriethoxysilane, n-octyltriethoxysilane, etc. are common coating chemicals to modify the surface of silica. The native and the surface-coated microcapsules thus provide adhesiveness to almost all of the common polymers, including polyethylene, polypropylene, polystyrene, polycarbonate, polyurethane, polybutadiene, polyethylene terephthalate, polybutylene terephthalate, polyoxymethylene, polymethacrylate, poly(methyl methacrylate), nylon, poly(vinyl chloride), ABS, polylactide, polyvinylidene chloride, and polyether ether ketone.

The surface of the microcapsules can be controlled from very smooth to very rough, which also depends on the parameters of the proprietary process. In addition to the roughness, the surface of the microcapsules can be kept native, which is covered by hydroxyl group and makes the microcapsules very adhesive to some hydrophilic resins and polymer blends; the surface can also be chemically modified to hydrophobic or covered by specific functional groups, which makes the microcapsules miscible with different types of hydrophobic plastics and blends, such as polyolefins and phenolics. The interior of the proprietary silica microcapsules can also load various chemicals, such as catalysts, fire retardant chemicals, and pigments. The native properties of silica itself, the unique properties of the proprietary silica microcapsules, and the additional properties of the encapsulants in the interior make the microcapsules, in the absence or presence of their encapsulants, very useful in the plastics additive industry.

The resulting powder products are silica microcapsules with a controllable size range from 0.1 μm to 1000 μm, and thus yielding a density range from 0.001 $g/cm^3$ to 1.0 $g/cm^3$. The density of the products is about 2.6 to 2640 times lower than silica itself (2.64 $g/cm^3$), 0.9 to 900 times lower than most of the plastic products (approximately 0.9 $g/cm^3$), and 1 to 1000 times lower than water (1.0 $g/cm^3$). The extremely low density property of the resultant products make these silica microcapsules ideal for density-reducing additives in the manufacturing of light-weight plastics, composites, rubbers and textile products just by introducing the silica microcapsules during the processing stage of these products. These lightweight products will greatly reduce the consumption of energy during transportation.

The present invention will be more readily understood by referring to the following examples which are given to illustrate the invention rather than to limit its scope.

Example 1

Canola Oil Droplets as Templates for the Preparation of Vinyl-Functionalized Silica Microcapsules Silica microcapsules are synthesized using oil-in-water (O/W) micro emulsion and sol-gel process. As oil phase, 60 g of TEOS is dissolved in 160 g of canola oil under stirring. Subsequently, the aqueous phase is prepared by dissolving 4 g (0.6 wt %) of Tween 80 and 40 g (6 wt %) of ethanol in 610 g of a chloridric acid solution at pH 1.2. The oil phase is emulsified in the aqueous phase at a stirring rate of 600 rpm on a Caframo Universal model BDC 3030 high torque overhead stirrer at room temperature for 20 minutes. The stirring rate is then lowered to 800 rpm and the emulsion is stirred at 40° C. for 2 hours. After overnight aging at room temperature, the obtained product is washed several times with deionized water, filtrated and dried. This affords a white powder of silica microcapsules covered by silanol functions with an average diameter of 230 μm.

For the post-functionalization step, the silica microcapsules powder is poured in a column, equipped with a heating system and a single neck flask containing the appropriate alkoxysilane. Prior to use, this assembly is purged for 10 minutes with argon. In the case of vinyl-functionalized silica microcapsules, the functionalization is performed using vinyltrimethoxysilane (VTMS) at 90° C. under vacuum. Then, reaction is allowed to proceed overnight.

Example 2

Heptanes Droplets as Templates for the Preparation of Aminopropyl-Functionalized Silica Microcapsules In a first step, 40 g of TEOS and 10 g of 3-aminopropyl triethoxysilane are dissolved in 150 g of heptanes under stirring. Subsequently, the aqueous phase is prepared by dissolving 4 g (0.7 wt %) of Pluronic 123 and 25 g (4.5 wt %) of ethanol in 554 g of an ammonia solution at pH 11.2. The emulsion is obtained by dispersing the oil phase in the aqueous solution at a stirring rate of 600 rpm using a Caframo Universal model BDC 3030 high torque overhead stirrer at room temperature, followed by stirring at 40° C. for 2 hours. After overnight aging at room temperature, the microcapsules are washed several times with deionized water and filtrated and dried. This affords a white powder of silica microcapsules covered by aminopropyl functions with an average diameter of 35 μm.

Example 3

Toluene Droplets as Templates for the Preparation of Silica Microcapsules 60 g of TEOS is dissolved in 160 g of toluene. The organic phase is emulsified in 630 g of ammonia solution at pH 11.3 containing 0.6% wt of TWEEN80 and 5% wt of glycerol, at a stirring rate of 600 rpm. The obtained emulsion is then stirred at 40° C. for 1 hour and allowed overnight to react at room temperature. The microcapsules are washed with deionized water and diethyl ether, filtrated and dried to give a white fine silica powder with an average particle diameter of 94 μm

Example 4

Water Droplets as Templates for the Preparation of Silica Microcapsules

The aqueous phase is prepared by dissolving 5 g (2.1%) of Pluronic 123 and 40 g (17.1%) of ethanol in 190 g of an ammonia solution at pH 11.5. The emulsion is obtained by dispersing the aqueous phase in an oil phase composed of 400 g hexanes at a stirring rate of 600 rpm at room temperature, followed by the addition 60 g of TEOS. The temperature is then raised to 40° C., with a stirring rate of 600 rpm for 2 hours. After overnight aging at room temperature, the microcapsules are washed several times with hexanes and deionized water and filtrated and dried. This affords a white powder of silica microcapsules with an average diameter of about 63 μm.

Example 5

Preparation of Silica Microcapsules Loaded with Octadecane

Octadecane, a phase change material, is encapsulated using oil-in-water (O/W) micro emulsion combined with sol-gel process. As oil phase, 60 g of TEOS and 70 g of octadecane are dissolved in 120 g of heptane under stirring. Subsequently, the aqueous phase is prepared by dissolving 4 g (0.7 wt %) of SPAN 80 and 30 g (5.3 wt %) of ethanol in 530 g of an ammonia solution at pH 11.6. The oil phase is emulsified in the aqueous phase at a stirring rate of 600 rpm on a Caframo Universal model BDC 3030 high torque overhead stirrer at room temperature for 2 hours. After overnight aging at room temperature, the obtained product is washed several times with deionized water, filtrated and dried. The product of this process consists of 45% (w/w) octadecane encapsulated in silica spheres of 30 to 77 μm.

Example 6

Preparation of Silica Microcapsules Loaded with a Cosmetic Oil

A commercially available cosmetic oil is encapsulated using oil-in-water (O/W) micro emulsion combined with sol-gel process. 70 g of TEOS and 60 g of cosmetic oil are dissolved in 125 g of heptane. The oil phase is emulsified in 630 g of ammonia solution at pH 11.3 containing 0.6% wt of TWEEN80 and 6% wt of ethanol, at a stirring rate of 600 rpm. The obtained emulsion is then stirred at 40° C. for 1 hour. After overnight aging at room temperature, the obtained product is washed several times with deionized water, filtrated and dried. The product of this process consists of 39% (w/w) cosmetic oil encapsulated in silica spheres of 10 to 30 μm.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A microcapsule comprising:
    a silica shell having a thickness of from about 50 nm to about 500 μm, and a plurality of pores,
    said shell forming a capsule having a diameter from about 0.2 μm to about 1500 μm, and having a density of about 0.001 g/cm$^3$ to about 1.0 g/cm$^3$,
    wherein said shell comprises from about 0% to about 70% Q3 configuration, and from about 30% to about 100% Q4 configuration, or
    wherein said shell comprises from about 0% to about 60% T2 configuration and from about 40% to about 100% T3 configuration, or
    wherein said shell comprises a combination of T and Q configurations thereof, and
    wherein an exterior surface of said microcapsule is covered by a functional group.

2. The microcapsule of claim 1, wherein said shell comprises about 40% Q3 configuration and about 60% Q4 configuration, or about 100% Q4 configuration.

3. The microcapsule of claim 1, wherein said pores have pore diameters from about 0.5 nm to about 100 nm.

4. The microcapsule of claim 1, further comprising a surface layer.

5. The microcapsule of claim 4, wherein said surface layer comprises a thickness from about 1 nm to about 10 nm.

6. The microcapsule of claim 4, wherein said surface layer is functionalized with an organosilane.

7. The microcapsule of claim 6, wherein said organosilane is chosen from a functional trimethoxysilane, a functional triethoxysilane, a functional tripropoxysilane, 3-aminopropyltriethoxysilane, vinyltriacetoxy silane, a vinyltrimethoxysilane, 3-glycidoxypropyltrimethoxysilane, 3-methacryloxypropyltrimethoxysilane, 3-chloropropyltriethoxysilane, a bis-(triethoxysilylpropyl)tetrasulfane, a methyltriethoxysilane, a n-octyltriethoxysilane, and a phenyltrimethoxysilane and combinations thereof.

8. The microcapsule of claim 4, wherein said surface layer is functionalized with a hydroxyl group, an amino group, a benzylamino group, a chloropropyl group, a disulfide group, an epoxy group, a mercapto group, a methacrylate group, a vinyl group, and combinations thereof.

9. The microcapsule of claim 1, further comprising a conductive layer surrounding said exterior surface of said capsule.

10. The microcapsule of claim 9, wherein said conductive layer is a metallic layer, or a conductive polymer layer.

11. The microcapsule of claim 10, wherein said metallic layer is a layer of silver (Ag), gold (Au), copper (Cu), aluminum (Al), or combinations thereof.

12. The microcapsule of claim 10, wherein said conductive polymer layer is a layer of polypyrrole, polythiophene, polyanilines or combinations thereof.

13. The microcapsule of claim 5, further comprising an active agent.

14. The microcapsule of claim 13, wherein said active agent is chosen from a catalyst for monomers polymerization, a polymer stabilizer chemical, a fire retardant chemical, a colorant, a pharmaceutically active drug, an enzyme, a cosmetic oil, a fragrance, a perfume, a food additives, an humidifier, an explosive, a phase change material (PCM), an insecticide, an herbicide, a fungicide and combinations thereof, and
    wherein said polymer stabilizer chemical is chosen from butylated hydroxytoluene (BHT), α-tocopherol, tocopheryl acetate, an organophosphate, Tris(2,4-di-tert-butylphenyl) phosphite, trisnonylphenyl phosphite, dilauryl thiodipropionate, distearyl thiodipropionate, Bis(2, 2,6,6-tetramethyl-4-piperidyl)sebacate, benzotriazoles, benzophenones and combinations thereof, and wherein said fire retardant chemical is chosen from tetrabromobisphenol-A, decabromodiphenylethane, dibromoneopentylglycol, or combinations thereof, and wherein said colorant is chosen from carbon black, molybdate orange, chrome oxide green, anthanthrone, anthraquinone, benzimidazole, and quinacridone.

15. The microcapsule of claim 13, wherein said active agent is crosslinked to said surface layer, to said exterior surface, or both.

16. The microcapsule of claim 13, wherein said active agent is encapsulated in said microcapsule.

17. The microcapsule of claim 1, having the NMR spectrum as shown in FIG. 1.

18. A process for the post-functionalization in solution of a microcapsule according to claim 1 comprising step a):
   a) dispersion, under inert atmosphere, of the dried silica microcapsules in a dried organic solvent in the presence of one or more organo-reactive silanes and an organic acid or an organic base for a time sufficient and at a temperature sufficient obtain a functionalized microcapsule in a liquid dispersion.

19. The process of claim 18, further comprising step b) after step a):
   b) separating said functionalized microcapsule from said liquid dispersion.

20. The process of claim 19, further comprising step c) after step b):
   c) drying said functionalized microcapsule to obtain a dried functionalized microcapsule.

* * * * *